US012708507B2

(12) United States Patent
Zielke

(10) Patent No.: US 12,708,507 B2
(45) **Date of Patent: *Aug. 18, 2026**

(54) VISCOELASTIC SOFT TIP PLUNGER

(71) Applicant: Alcon Inc., Fribourg (CH)

(72) Inventor: Mark Andrew Zielke, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 190 days.

This patent is subject to a terminal disclaimer.

(21) Appl. No.: 18/643,986

(22) Filed: Apr. 23, 2024

(65) Prior Publication Data

US 2024/0268952 A1 Aug. 15, 2024

Related U.S. Application Data

(63) Continuation of application No. 16/905,738, filed on Jun. 18, 2020, now Pat. No. 11,998,445.

(Continued)

(51) Int. Cl.
*A61F 2/16* (2006.01)

(52) U.S. Cl.
CPC ............ *A61F 2/167* (2013.01); *A61F 2/1678* (2013.01); *A61F 2002/1683* (2013.01); *A61F 2002/16905* (2015.04)

(58) Field of Classification Search
CPC .................... A61F 2/167; A61F 2/1678; A61F 2002/1683; A61F 2002/16905; A61F 2/1664; A61F 9/00736; A61F 2009/00887
See application file for complete search history.

(56) References Cited

U.S. PATENT DOCUMENTS 11,998,445 B2 * 6/2024 Zielke .................. A61F 2/1678
2009/0248141 A1 10/2009 Shandas et al.

(Continued)

FOREIGN PATENT DOCUMENTS

JP 2002011092 A 1/2002
WO 2017106028 A1 6/2017

(Continued)

OTHER PUBLICATIONS

Chen, Song et al., Complete Collection of Operative Surgery: Ophthalmic Surgery (Second Edition), People's Military Medical Press, Sep. 30, 2008, p. 411.

(Continued)

*Primary Examiner* — Ashley L Fishback
*Assistant Examiner* — Chima U Igboko
(74) *Attorney, Agent, or Firm* — Patterson + Sheridan, LLP

(57) ABSTRACT

Systems, methods, and devices for inserting an intraocular lens (IOL) assembly into an eye may be provided. An apparatus for delivery of a lens component into an eye may include a housing. The apparatus may further include a plunger at least partially disposed in the housing, wherein the housing comprises an elongated portion and a viscoelastic soft tip at a distal end of the elongated portion, wherein the viscoelastic soft tip has a storage modulus of about 1 megapascal (MPa) to about 300 MPa and a loss module of about 1 MPa to about 300 MPa. The apparatus may further include a drive mechanism operatively coupled to plunger and configured to cause the plunger to translate in the housing. The apparatus may further include a nozzle operatively coupled to the housing through which the plunger delivers the lens component into the eye.

20 Claims, 6 Drawing Sheets

Related U.S. Application Data

(60) Provisional application No. 62/873,224, filed on Jul. 12, 2019.

(56) References Cited

U.S. PATENT DOCUMENTS

2010/0305577 A1* 12/2010 Muchhala ............. A61F 2/1678
606/107
2016/0015511 A1* 1/2016 Auld ....................... A61F 2/167
606/107

FOREIGN PATENT DOCUMENTS

WO 2018211416 A1 11/2018
WO 2019113077 A1 6/2019

OTHER PUBLICATIONS

Chenge, Wang, Plastics Tribology: Theory and Practice of Friction, Wear, and Lubrication of Plastics, Mechanical Industry Press, Dec. 31, 1994, pp. 217-218.

* cited by examiner

VISCOELASTIC SOFT TIP PLUNGER

CROSS-REFERENCE TO RELATED APPLICATIONS

This application is a continuation of U.S. patent application Ser. No. 16/905,738, filed on Jun. 18, 2020, which claims priority to and benefit of U.S. Provisional Patent Application No. 62/873,224, filed Jul. 12, 2019, the entire contents of which are incorporated by reference herein in their entirety.

TECHNICAL FIELD

The present disclosure may generally relate to eye surgery and, more particularly, embodiments may generally relate to systems, methods, and devices for inserting an intraocular lens (IOL) that employ a plunger having a viscoelastic soft tip.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. To avoid damaging the IOL, the plunger may include a soft tip. These soft tip plungers should be gentle on the IOL even where large amounts of force can be required to push the IOL through the nozzle of the insertion tool. However, the use of soft tip plungers can have drawbacks. As the soft tip plunger moves through the nozzle in engagement with the IOL, the soft tip can compress, storing spring energy. Upon exit from the nozzle, the soft tip can rapidly expand releasing the spring energy. Since the soft tip is engagement with the IOL, this spring energy can be transferred to the IOL leading to a sudden or self-ejection of the IOL from the nozzle, which is highly undesirable and can lead to complications as the insertion IOL into the eye should be performed in a controlled manner.

SUMMARY

In an exemplary embodiment, the present disclosure provides an apparatus for delivery of a lens component into an eye. The apparatus may include a housing and a plunger at least partially disposed in the housing, wherein the housing comprises an elongated portion and a viscoelastic soft tip at a distal end of the elongated portion, wherein the viscoelastic soft tip has a storage modulus of about 1 megapascal (MPa) to about 300 MPa and a loss module of about 1 MPa to about 300 MPa. The apparatus may further include a drive mechanism operatively coupled to plunger and configured to cause the plunger to translate in the housing. The apparatus may further include a nozzle operatively coupled to the housing through which the plunger delivers the lens component into the eye.

In another exemplary embodiment, the present disclosure provides a method for delivery of a lens component into an eye. The method may include inserting a nozzle of an insertion tool into the eye. The method may further include actuating the insertion tool to move a plunger through the nozzle such that the plunger drives a lens component through the nozzle and into the eye, wherein a viscoelastic soft tip of the plunger engages the lens component, wherein the viscoelastic soft tip has a storage modulus of about 1 MPa to about 300 MPa and a loss module of about 1 MPa to about 300 MPa. The method may further include placing lens component with a capsular bag in the eye.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
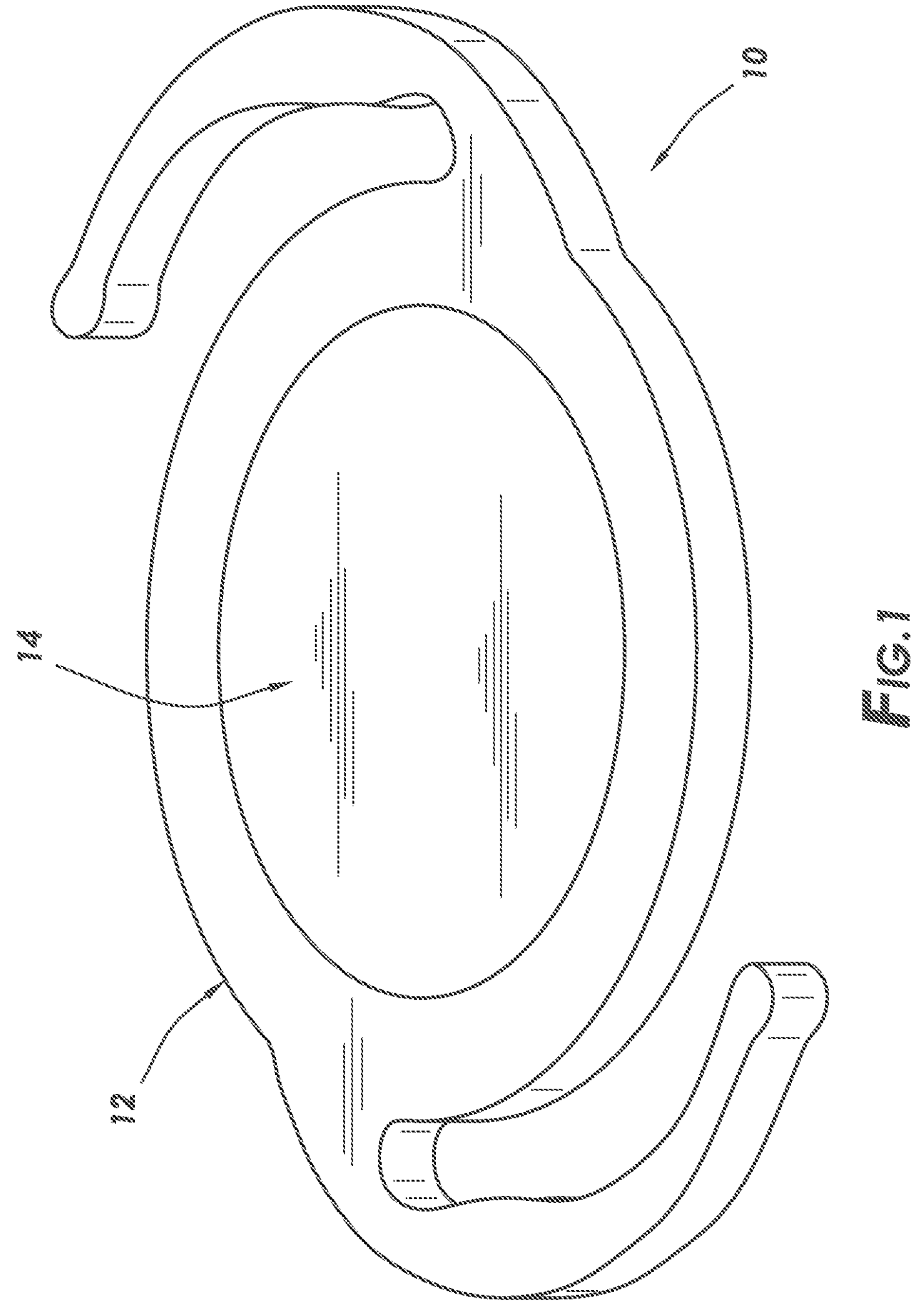
FIG. 1 illustrates a modular IOL with the lens portion positioned in the base portion in accordance with embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates.

In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments may generally relate to eye surgery. More particularly, embodiments may generally relate to systems, methods, and devices for inserting an intraocular lens (IOL). Embodiments may include an insertion tool for preparation and delivery of the IOL assembly into a patient's eye that includes a plunger, a nozzle, and an IOL holder. Embodiments of the IOL may include a modular IOL that includes a base portion and a lens portion. In some embodiments, the plunger may include a viscoelastic soft tip. The viscoelastic soft tip may engage a lens component and drive the lens component through the nozzle. The lens component may be the IOL itself or an individual component of a modular IOL, such as a base portion of a lens portion. Advantageously, the viscoelastic soft tip should reduce the tendency for a soft tip plunger to have an undesirable sudden or self-ejection of the IOL, for example, due to release of spring energy stored from compression of the soft tip. By proper selection of the viscoelastic properties of the viscoelastic soft tip, the stored spring energy should be slowly released, thus reducing, or potentially even eliminating, the undesirable sudden and self-ejection of the IOL.

FIG. 1 illustrates an embodiment of a modular IOL 10. The modular IOL 10 may be any suitable modular interocular lens. As illustrated, the modular IOL 10 may include a base portion 12 and a lens portion 14. In the illustrated embodiment, the lens portion 14 is positioned in the base portion 12. In operation, the modular IOL 10 can allow for the lens portion 14 to be modified or adjusted while leaving the base portion 12 in place, either intra-operatively or post-operatively. By way of example, the modular IOL 10 may be implanted into an eye. After implantation, the lens portion 14 may be modified, adjusted, and/or replaced while leaving the base portion 12 positioned in the eye. In at least one embodiment, the modular IOL 10 may be assembled in the eye. For example, the base portion 12 may first be implanted in the eye. The lens portion 14 may then be delivered into the eye and attached to the base portion 12.

Figure 2:
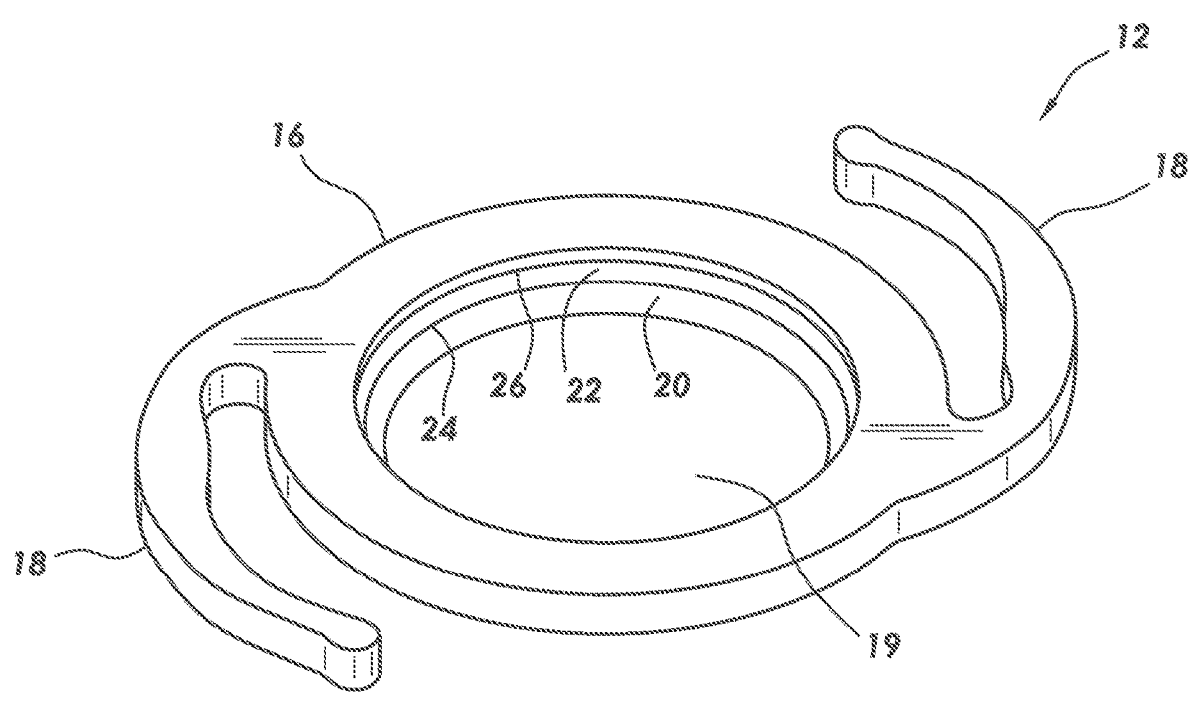
FIG. 2 illustrates a base portion of a modular IOL in accordance with embodiments of the present disclosure.

FIG. 2 illustrates the base portion 12 of the modular IOL 10 of FIG. 1 in accordance with embodiments of the present disclosure. In the illustrated embodiment, the base portion 12 includes a base 16 and haptic extensions 18. The haptic extensions 18 may be arms (or other suitable extensions) extending from the base 16 that may stabilize the base portion 12 when it may be disposed within the patient's eye. In the illustrated embodiment, the base 16 may define a hole 19, which may be centrally located in the base 16 as shown on FIG. 2. While the hole 19 is shown as a through hole extending through the base 16, embodiments also contemplate hole 19 being a blind hole that does not extend through the base 16. For example, the base 16 may be a solid disc with the hole 19 being a blind hold that does not extend through the base 16, rather than an annular ring with the hole 19 extending through the base 16. Hole 19 may be defined by inner perimeter surface 20 of the base 16. In at least one embodiment, a recessed groove 22 is formed in inner perimeter surface 20. Recessed groove 22 may include a lower rim 24 and an upper rim 26. The upper rim 26 may have an insider diameter that is the same as or greater than the outside diameter of the lens portion 14 (excluding tabs 30 shown on FIG. 3) such that the lens portion 14 can rest inside the hole 19 of the base 16. All or a portion of the lower rim 24 can have an inside diameter that is less than the outside diameter of the lens portion 14 (excluding tabs 30 shown on FIG. 3) such that the lower rim 24 can act as a ledge or backstop for the lens portion 14 when placed in the hole 19 of the base 16. The base portion 12 may be unitary or may be formed from component parts that are combined or attached in any suitable manner.

Figure 3:
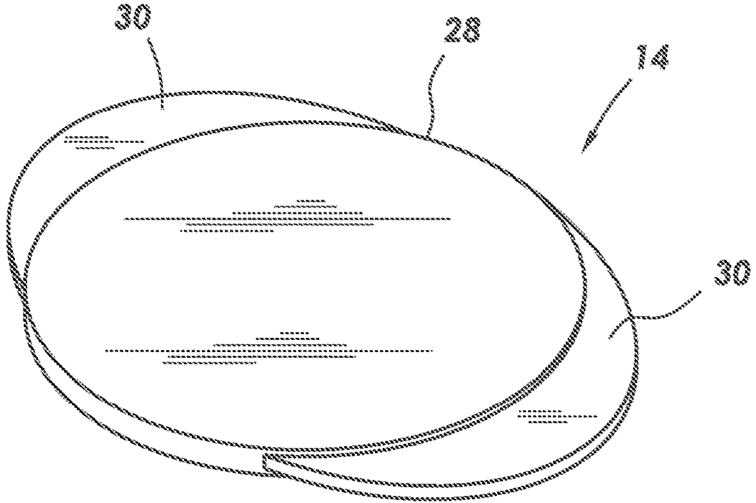
FIG. 3 illustrates a lens portion of a modular IOL in accordance with embodiments of the present disclosure.

With reference to FIG. 3, the lens portion 14 of the modular IOL 10 of FIG. 1 is illustrated in accordance with embodiments of the present disclosure. In the illustrated embodiments, the lens portion 14 includes an optic portion 28 and one or more tabs 30. While FIG. 3 illustrates two of the tabs 30, embodiments may include only one of the tabs 30 or alternatively three, four, or more of the tabs 30. In addition, the tabs 30 on the lens portion 14 may be the same or different from one another. The tabs 30 are shown as being fixed to the optic portion 28; however, it should be understood that one or more of the tabs 30 may be actuated to move from a compressed position for delivery into the hole 19 of the base 16 (e.g., shown on FIG. 2) to an uncompressed extended position for deployment into the recessed groove 22 of the base 16 (e.g., shown on FIG. 2), thus forming an interlocking connection between the base portion 12 and the lens portion 14. The outside curvature of the tabs 30 may have a radius conforming to the inside radius of the recessed groove 22. This arrangement should limit relative movement between the base portion 12 and the lens portion 14 once connected. In embodiments, a suitable optic portion 28 may be in a shape similar to that of a natural lens within the eye and made from a suitable material such as silicone, acrylic, and/or combinations thereof. While the optic portion 28 is shown as being circular, the optic portion 28 may be any suitable shape, such as oval or ellipsoidal, for example, with the tabs 30 positioned adjacent the long axis. This arrangement would thus define a gap between the edge of the optic portion 28 along its short axis and the inner perimeter surface 20 in the base 16. The gap may enable access for a probe or similar device to pry apart the lens portion 14 from the base portion 12 if separation were needed.

Figure 4:
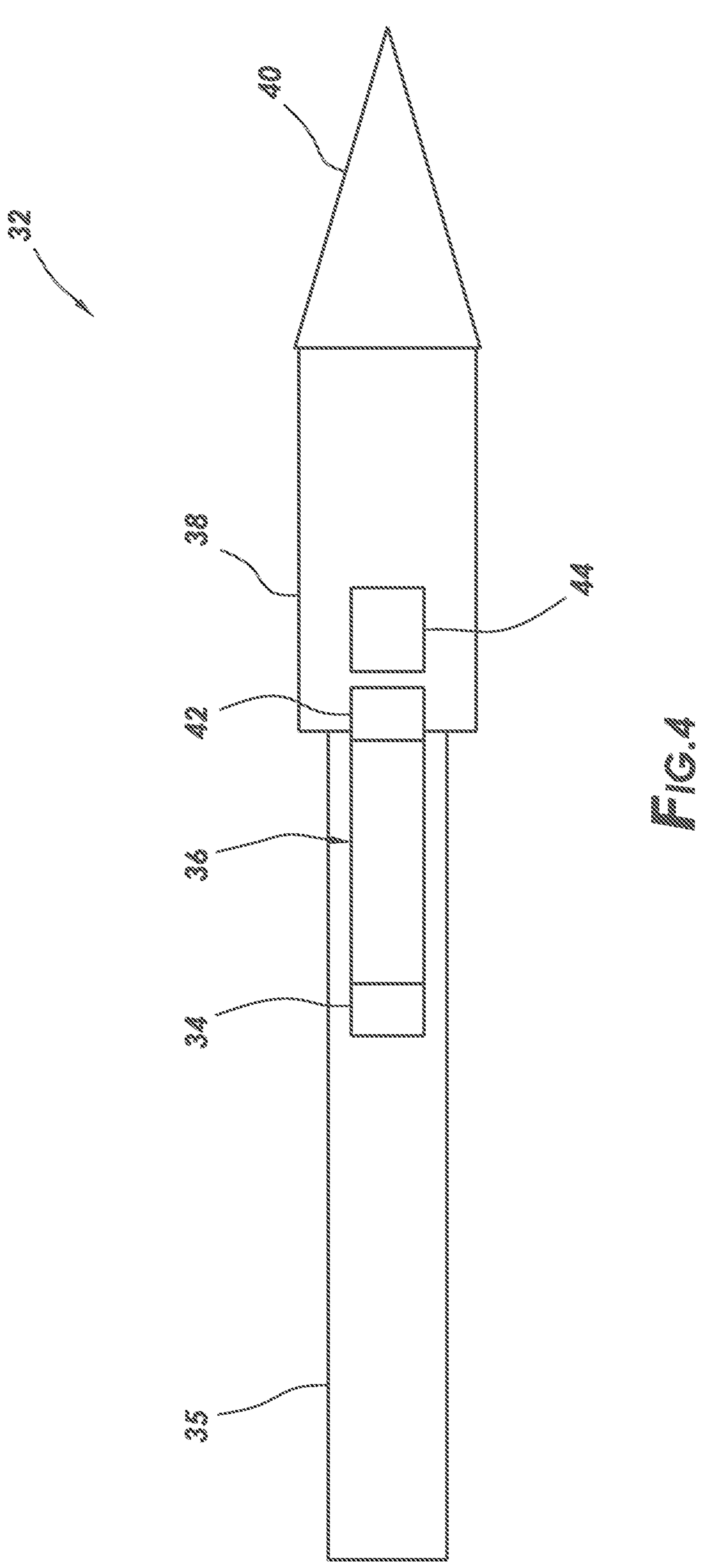
FIG. 4 illustrates an insertion tool in accordance with embodiments of the present disclosure.

FIG. 4 illustrates a schematic of an insertion tool 32. In some embodiments, the insertion tool 32 may include a drive mechanism 34, a plunger 36, a lens holder 38, and a nozzle 40. The plunger 36 may be disposed at least partially in a housing 35. For example, plunger 36 may extend from housing 35 to engage the drive mechanism 34 outside the housing 35. In other embodiments, the plunger 36 may disposed within the housing 35. In some embodiments. The drive mechanism 34 may be operatively coupled to the plunger. As illustrated, the plunger 36 may include a viscoelastic soft tip 42. The insertion tool 32 may be operable for delivery of a lens component 44 into a patient's eye. The lens component 44 may include any suitable component of an IOL, including the IOL itself or a component of the modular IOL 10 shown on FIG. 2, such as the base portion 12 or the lens portion 14.

The drive mechanism 34 may be any suitable combination of components to actuate the plunger 36. For example, the drive mechanism 34 may utilize a lever and/or pneumatic systems. The plunger 36 may be operatively coupled to the drive mechanism 34. The drive mechanism 34 may actuate the plunger 36 through any suitable technique including, but not limited to, an electric drive, a mechanical drive, a hydraulic drive, a pneumatic drive, and/or combinations thereof. The plunger 36 may be actuated to move through the lens holder 38. The lens holder 38 may be disposed at any suitable location within the insertion tool 32, for example, the lens holder 38 may be contained in or inserted into the housing 35 through which the plunger 36 is driven. In some embodiments, the lens holder 38 may be located between the drive mechanism 34 and the nozzle 40. In some embodiments, the lens holder 38 may contain a lens component 44. In some embodiments, the lens component 44 may be loaded in the lens holder 38 in an unfolded configuration. The lens holder 38 may be actuated to fold the lens component 44 for delivery the nozzle 40. As used herein, folding of the lens component 44 is also intended to encompass rolling of the lens component 44. For example, the haptic extensions 18 of the base portion 12 shown on FIG. 2 may be folded onto the base 16, which may then be folded or rolled. By way of further example, the lens portion 14 shown on FIG. 2 may be folded or otherwise rolled into a folded configuration for delivery through the nozzle 40. As the plunger 36 moves through the lens holder 38, the plunger 36 may displace the lens component 44 through the nozzle 40. The viscoelastic soft tip 42 should engage the lens component 44 as it moves through the nozzle 40.

In some embodiments, the insertion tool 32 may be preloaded. That is, when provided to an end-user, the insertion tool 32 may have a lens component 44 (e.g., modular IOL 10, base portion 12, or lens portion 14) in an unfolded state already present there within and ready to deliver. Having the insertion tool 32 preloaded with the lens component 44 should reduce the number of steps a user may be required to accomplish before delivering the lens component 44 into a patient. With a reduced number of steps, error and risk associated with delivery of the lens component 44 into a patient may be reduced. Further, an amount of time required to deliver the lens component 44 may also be reduced. In some embodiments, the lens component 44 may be pre-loaded into the lens holder 38.

Figure 5A:
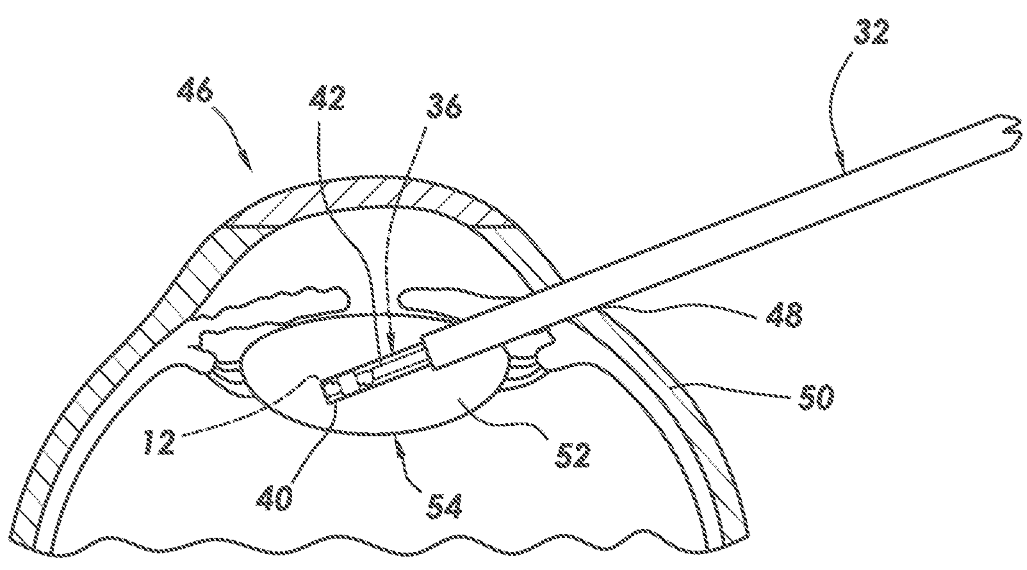
FIGS. 5A-5C illustrate implantation of a modular IOL in accordance with embodiments of the present disclosure.
Figure 5B:
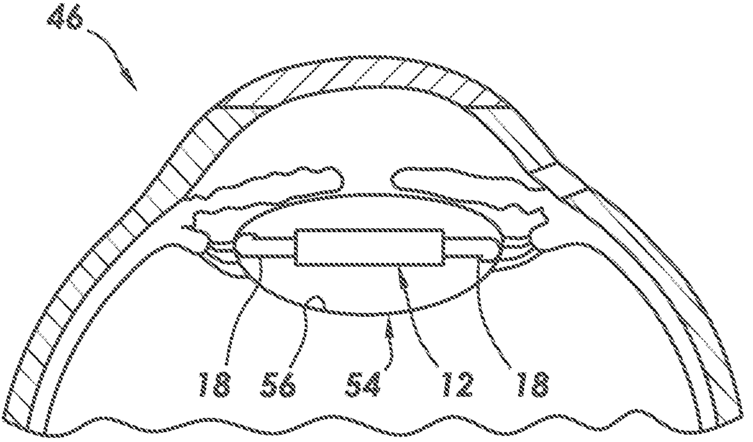

An example technique for implantation of the modular IOL 10 into an eye 46 of a patient will now be described with respect to FIGS. 5A to 5C. As illustrated on FIG. 5A, the insertion tool 32 may first dispense the base portion 12 into the eye 46 of a patient. In embodiments, an incision 48 may be made in the eye 46 by a surgeon. For example, the incision 48 may be made through the sclera 50 of the eye 46. The incision 48 may be a suitable width or length. Without limitation, the suitable width and/or length may be less than about 4 millimeters. For example, the incision 48 may have a suitable width and/or length of from about 1 millimeter to about 4 millimeters, about 1 millimeter to about 3 millimeters, from about 2 millimeters to about 3 millimeters, or from about 2 millimeters to about 2.5 millimeters. After the incision 48 is made, the nozzle 40 of the insertion tool 32 may be inserted through the incision 48 into an interior portion 52 of the eye 46. The insertion tool 32 may be actuated to dispense the base portion 12 into a capsular bag 54 of the eye 46. For example, the plunger 36 with the viscoelastic soft tip 42 may engage the base portion 12 to drive the base portion 12 (in a folded (or rolled) configuration) through the nozzle 40 and into the interior portion 52 of the eye 46. Upon dispensation, the base portion 12 should unfurl and settle within the capsular bag 54 of the eye 46, as shown on FIG. 5B. The haptic extensions 18 may be manipulated, for example, to engage the inside equator 56 of the capsular bag 54. The haptic extensions 18 may engage the capsular bag 54 to secure the base portion 12 in the capsular bag 54.

Figure 5C:
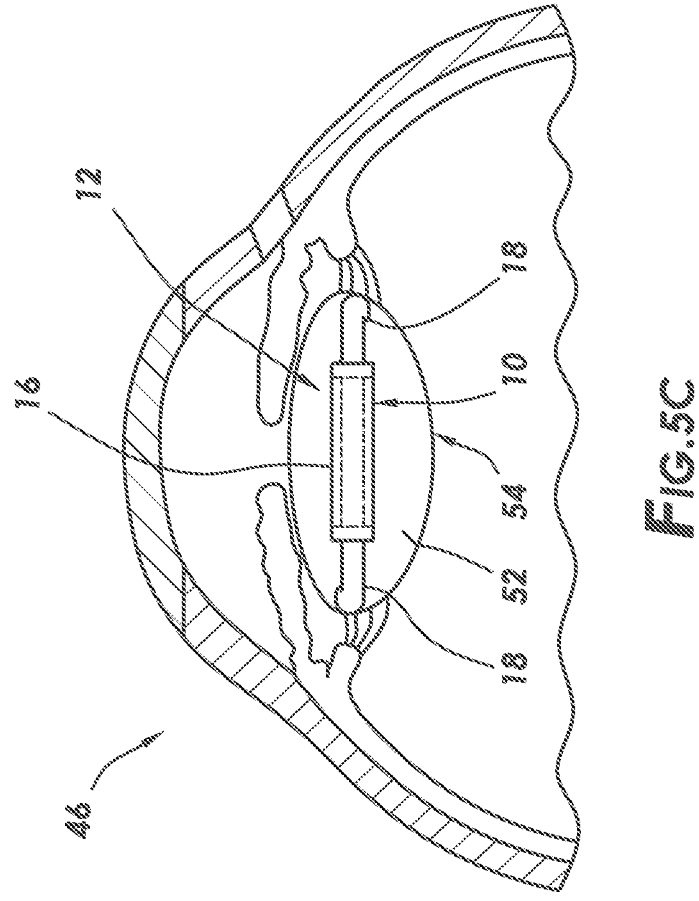

As illustrated on FIG. 5C, the lens portion 14 may be positioned in the interior portion 52 of the eye 46. In the illustrated embodiment, the lens portion 14 is shown positioned in the base 16 of the base portion 12. While not shown on FIG. 5C, the inserter tool 32 shown on FIG. 5A or other suitable inserter may be used for delivery of the lens portion 14 into the eye 46. The lens portion 14 may be delivered in a folded (or rolled configuration) and allowed to unfurl after ejection from the inserter. The lens portion 14 may be positioned in the base 16 of the base portion 12 and secured to the base portion 12, for example, by use of the tabs 30 shown on FIG. 3, to form the modular IOL 10. However, embodiments should not be limited to use of the tabs 30 for interlocking the lens portion 14 and the base portion 12 and other suitable locking mechanisms may be used for securing lens portion 14 to the base portion 12 for forming the modular IOL 10. The base portion 12 may hold the lens portion 14 within the eye 46 so that the lens portion 14 may refract light to be focused on the retina (not shown).

Figure 6:
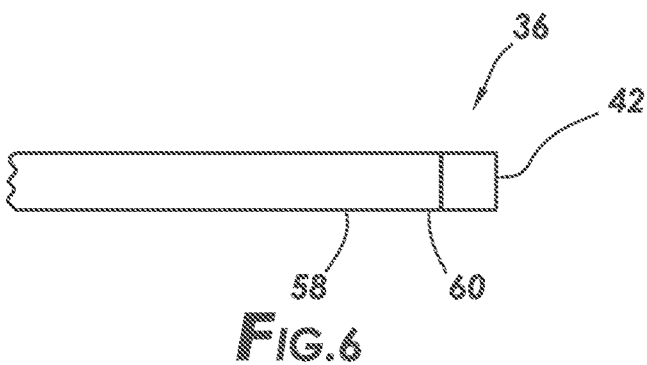
FIG. 6 illustrates a plunger having a viscoelastic soft tip in accordance with embodiments of the present disclosure.

FIG. 6 illustrates the plunger 36 in accordance with embodiments of the present disclosure. In the illustrated embodiment, the plunger 36 includes an elongated portion 58 and a viscoelastic soft tip 42. The elongated portion 58 may be formed from any suitable material. For example, suitable materials for the elongated portion 58 may include, for example, a metal, such as stainless steel or titanium. However, the elongated portion 58 may be formed from any suitable material, including, but not limited to, a polymer, metal, ceramic, or other suitable material. The viscoelastic soft tip 42 may be coupled at a distal end 60 of the elongated portion 58. Any suitable technique may be used for coupling the viscoelastic soft tip 42 and the elongated portion 58. For example, coupling the viscoelastic soft tip 42 and the elongated portion 58 may be accomplished with extrusion, casting, molding, injection molding, insert molding, welding, adhesives, or other desired or suitable methods. In some embodiments, the coupling may be accomplished using a combination of two or more of these methods. In some embodiments (not shown), the viscoelastic soft tip 42 and the elongated portion 58 may be unitary with the viscoelastic soft tip 42 being an extension of the elongated portion 58.

The elongated portion 58 may have any suitable dimensions. For example, the elongated portion 58 may have a length of about 0.5 centimeters to about 10 centimeters. By way of further example, the elongated portion 58 may have an outer diameter of about 0.05 centimeters to about 0.3 centimeters. The viscoelastic soft tip 42 may also have any suitable dimensions. For example, the viscoelastic soft tip 42 may have a length of about 0.2 centimeters to about 1 centimeter. By way of further example, the viscoelastic soft tip 42 may have an outer diameter of about 0.1 centimeters to about 0.8 centimeters. Further, an exterior size and shape of the viscoelastic soft tip 42, in some embodiments, may correspond to the size and shape of the elongated portion 58, thereby producing a smooth transition between the elongated portion 58 and the viscoelastic soft tip 42.

The viscoelastic soft tip 42 may be adapted to provide a cushioning and/or non-abrasive engagement with lens component 44 (e.g., shown on FIG. 4), such as the base portion 12 (e.g., shown on FIG. 2) or the lens portion 14 (e.g., shown on FIG. 3). Thus, the hardness of the viscoelastic soft tip 42 may be selected, for example, to provide for a cushioning and/or non-abrasive engagement with the lens component 44. For example, the material forming the viscoelastic soft tip 42 may have a durometer value of 20 Å on the Shore hardness scale. In other instances, the material forming the viscoelastic soft tip 42 may have a durometer value of about 20 OO to 50 D on the Shore hardness scale. As used herein, durometer values are Shore hardness values. However, the disclosure is not so limiting. Rather, these hardness values are provided merely as examples. Thus, the material forming the viscoelastic soft tip 42 may have any suitable hardness as desired for a particular application.

In addition to hardness, the viscoelastic soft tip 42 may also be characterized by viscoelasticity. For example, the viscoelastic soft tip 42 may be exhibit both viscous and elastic characteristics when undergoing deformation. Due to pressure applied when forcing the lens component 44 through the nozzle 40 (e.g., shown on FIG. 4), the viscoelastic soft tip 42 can deform, for example, compress as it is forced through the nozzle 40 in engagement with the lens component 44. By having elastic characteristics, the viscoelastic soft tip 42 should return to its original state once the stress is removed, for example, after exit from the nozzle 40. However, if the viscoelastic soft tip 42 does not include sufficient viscous properties, the viscoelastic soft tip 42 can return to its original state too quickly thus undesirably pushing lens component 44 as the viscoelastic soft tip 42 springs back to its original state. Accordingly, embodiments may include selection of the viscous properties so that the viscoelastic soft tip 42 should slowly return to its original state without undesired auto ejection of the lens component caused by spring back to its original state too quickly.

The viscoelasticity of the viscoelastic soft tip 42 may be characterized by its storage (or elastic) modulus (G') and loss modulus (G"). By way of example, the storage modulus and the loss modulus of the viscoelastic soft tip 42 may be selected to provide desired viscoelasticity. Suitable storage modulus for the viscoelastic soft tip 42 at room temperature (23° C.) may range from about 1 megapascal (MPa) to about 300 MPa, from about 1 MPa to about 10 MPa, from about 10 MPa to about 50 MPa, or from about 50 MPa to about 300 MPa. For example, the viscoelastic soft tip 42 may have a storage modulus at room temperature (23° C.) of about 1 MPa, about 10 MPa, about 30 MPa, about 50 MPa, about 100 MPa, about 200 MPa, or about 300 MPa. Suitable loss modulus for the viscoelastic soft tip 42 at room temperature (23° C.) may range from about 1 MPa to about 300 MPa, from about 1 MPa to about 10 MPa, from about 10 MPa to about 50 MPa, or from about 50 MPa to about 300 MPa. For example, the viscoelastic soft tip 42 may have a loss modulus at room temperature (23° C.) of about 1 MPa, about 10 MPa, about 30 MPa, about 50 MPa, about 100 MPa, about 200 MPa, or about 300 MPa. As used herein, storage modulus and loss modulus are measured at a frequency of 1 Hz using the standardized test procedure described in ASTM D 4065 for Dynamic Mechanical Analysis ("DMA"). One of ordinary skill in the art with the benefit of this disclosure should be able to select appropriate storage modulus and loss modulus for the viscoelastic soft tip 42 for a particular application.

In accordance with present embodiments, the viscoelastic soft tip 42 may be formed from any suitable viscoelastic material. Particularly, in some embodiments, the viscoelastic soft tip 42 may be formed from any medically compatible viscoelastic material. The viscoelastic soft tip 42 may be formed from materials including, for example, polyurethane, acetate, acrylate, polyester, polyamide, and combinations thereof. In some embodiments, the viscoelastic soft tip 42 may comprise a viscoelastic polymer. Foams of the same material classes may be considered as well. In some embodiments, the elongated portion 58 and the viscoelastic soft tip 42 may comprise the same or similar materials.

Figure 7:
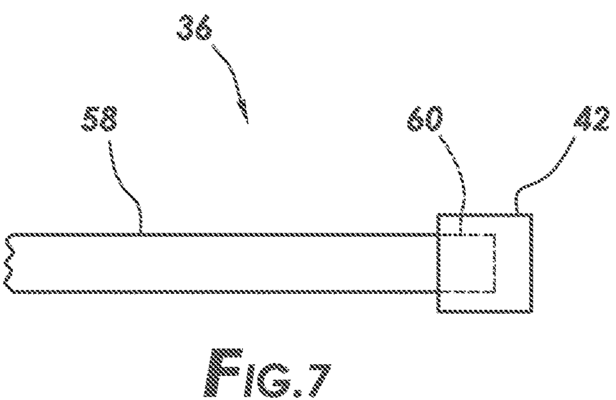
FIG. 7 illustrates another example of a plunger having a viscoelastic soft tip in accordance with embodiments of the present disclosure.

FIG. 7 illustrates the plunger 36 in accordance with another embodiment of the present disclosure. In the illustrated embodiment, the plunger 36 includes an elongated portion 58 and a viscoelastic soft tip 42. In contrast to the viscoelastic soft tip 42 shown on FIG. 6, the viscoelastic soft tip 42 is disposed around the distal end 60 of the plunger 36. Any suitable technique may be used for disposing the viscoelastic soft tip 42 around the distal end 60 of the plunger 36, including, but not limited to, extrusion, casting, molding, injection molding, insert molding, welding, adhesives, or other desired or suitable methods. In some embodiments, two or more of these methods may be used for attaching the viscoelastic soft tip 42 around the distal end 60 of the plunger 36.

Figure 8:
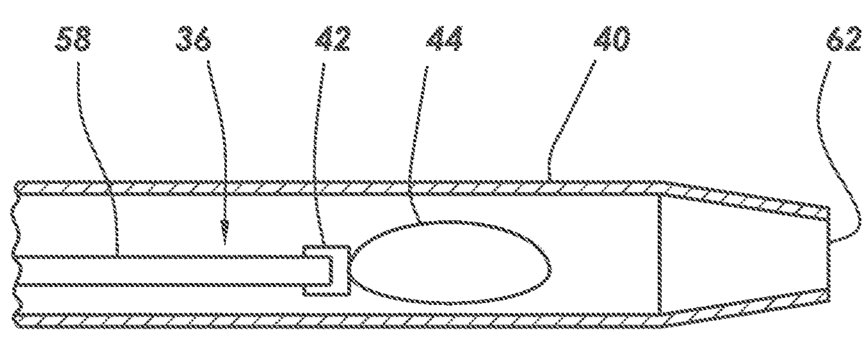
FIG. 8 illustrates a plunger having a viscoelastic soft tip pushing a lens component through a nozzle in accordance with embodiments of the present disclosure.
Figure 9:
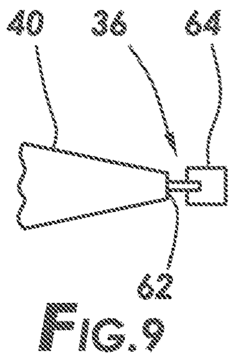
FIG. 9 illustrates a plunger having a soft tip after exit of the soft tip from the nozzle.
Figure 10:
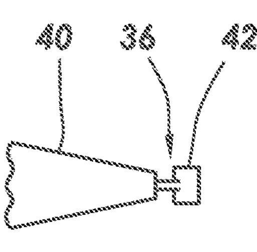
FIG. 10 illustrates a plunger having a viscoelastic soft tip after exit of the viscoelastic soft tip from the nozzle in accordance with embodiments of the present disclosure.

FIG. 8 illustrates a plunger 36 having a viscoelastic soft tip 42 pushing a lens component 44 through a nozzle 40 in accordance with embodiments of the present disclosure. As illustrated, the plunger 36 may include a viscoelastic soft tip 42 at its distal end 60. In the illustrated embodiment, the viscoelastic soft tip 42 engages the lens component 44 to push the lens component 44 through the nozzle 40. Due to the force required to force the viscoelastic soft tip 42 and lens component 44 through the nozzle 40, the viscoelastic soft tip 42 can compress or otherwise deform. As a result of this deformation, the viscoelastic soft tip 42 can store spring energy. The viscoelastic soft tip 42 should be advanced through the nozzle 40 until the lens component 44 is ejected from nozzle outlet 62. By tuning the viscoelasticity of the viscoelastic soft tip 42, the stored spring energy should not be undesirably released upon release of this compressive force when the viscoelastic soft tip 42 exits the nozzle outlet 62. As a result, problems typically associated with a soft tip resulting in undesirable sudden and self-ejection of the lens component 44 can be reduced or potentially even avoided from use of the viscoelastic soft tip 42. Additionally, as shown in FIG. 9, a plunger 36 having a soft tip 64 without tuning of viscoelasticity may rapidly expand after exit from the nozzle outlet 62, thus preventing retraction of the soft tip 64 into the nozzle 40 for exit from the patient's eye. However, as shown in FIG. 10, the plunger 36 having a viscoelastic soft tip 42 should slowly expand after exit from the nozzle outlet 62, allowing retraction into the nozzle 40 so that the nozzle 40 can be removed from the patient's eye.

While the preceding description is generally directed to use of the plunger 36 having a viscoelastic soft tip 42 (e.g., shown on FIG. 6 or 7) with a modular IOL 10 (e.g., shown on FIG. 1), it is contemplated that the viscoelastic soft tip 42 can be used in any suitable application for delivery of lens components, such as lens component 44 (e.g., FIG. 4). While the lens component 44 can be a modular IOL 10 are particular component thereof (e.g., base portion 12 on FIG. 2 or lens portion 14 on FIG. 3), the lens component 44 can also comprise a non-modular IOL in which base and the lens portions of the IOL are fixed to another where the lens portion cannot be exchanged without removal of the It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for intraocular lens delivery, comprising:
- a housing;
- a plunger at least partially disposed in the housing, wherein:
  - the plunger comprises an elongated portion and a viscoelastic soft tip at a distal end of the elongated portion, the viscoelastic soft tip has a storage modulus of about 1 megapascal to about 300 megapascals at 23 degrees Celsius, and the viscoelastic soft tip has a loss modulus of about 1 megapascal to about 300 megapascals at 23 degrees Celsius;

a pre-loaded lens in the housing;

a drive mechanism operatively coupled to the plunger and configured to cause the plunger to translate in the housing; and a nozzle operatively coupled to the housing through which the plunger delivers the pre-loaded lens into an eye.

2. The apparatus of claim 1, wherein the viscoelastic soft tip is disposed around the distal end of the elongated portion.

3. The apparatus of claim 1, wherein the viscoelastic soft tip comprises a viscoelastic polymer.

4. The apparatus of claim 1, wherein the viscoelastic soft tip comprises at least one material selected from the group consisting of polyurethane, acetate, acrylate, polyester, polyamide, foams thereof, and combinations thereof.

5. The apparatus of claim 1, wherein the pre-loaded lens is a non-modular lens.

6. The apparatus of claim 1, wherein the pre-loaded lens is a modular lens.

7. The apparatus of claim 1, wherein the viscoelastic soft tip has a durometer value of about 20 OO to about 50 D on a Shore hardness scale.

8. The apparatus of claim 1, wherein the storage modulus of the viscoelastic soft tip is about 10 megapascals to about 50 megapascals.

9. The apparatus of claim 1, wherein the loss modulus of the viscoelastic soft tip is about 10 megapascals to about 50 megapascals.

10. The apparatus of claim 1, wherein the drive mechanism is an electric drive, a mechanical drive, a hydraulic drive, a pneumatic drive, or a combination thereof.

11. An apparatus for intraocular lens delivery, comprising:

a housing;

a plunger at least partially disposed in the housing, wherein:

the plunger comprises an elongated portion and a viscoelastic soft tip at a distal end of the elongated portion, the viscoelastic soft tip has a storage modulus of about 1 megapascal to about 300 megapascals at 23 degrees Celsius, and the viscoelastic soft tip has a loss modulus of about 1 megapascal to about 300 megapascals at 23 degrees Celsius;

a lens holder coupled to the housing;

a pre-loaded lens in the lens holder;

a drive mechanism operatively coupled to plunger and configured to cause the plunger to translate in the housing; and a nozzle operatively coupled to the housing through which the plunger delivers the pre-loaded lens into an eye.

12. The apparatus of claim 11, wherein the pre-loaded lens is a non-modular lens.

13. The apparatus of claim 11, wherein the pre-loaded lens is a modular lens.

14. The apparatus of claim 11, wherein the viscoelastic soft tip has a durometer value of about 20 OO to about 50 D on a Shore hardness scale.

15. The apparatus of claim 11, wherein the storage modulus of the viscoelastic soft tip is about 10 megapascals to about 50 megapascals.

16. The apparatus of claim 11, wherein the loss modulus of the viscoelastic soft tip is about 10 megapascals to about 50 megapascals.

17. An apparatus for intraocular lens delivery, comprising:

a housing;

a plunger at least partially disposed in the housing, wherein:

the plunger comprises an elongated portion and a viscoelastic soft tip at a distal end of the elongated portion, the viscoelastic soft tip has a storage modulus of about 10 megapascals to about 50 megapascals at 23 degrees Celsius, the viscoelastic soft tip has a loss modulus of about 10 megapascals to about 50 megapascals at 23 degrees Celsius, and the viscoelastic soft tip comprises at least one material selected from the group consisting of acetate, acrylate, polyester, polyamide, foams thereof, and combinations thereof;

a pre-loaded lens in the housing;

a drive mechanism operatively coupled to the plunger and configured to cause the plunger to translate in the housing; and a nozzle operatively coupled to the housing through which the plunger delivers the pre-loaded lens into an eye, wherein the viscoelastic soft tip provides cushioning and non-abrasive engagement with the pre-loaded lens during translation of the drive mechanism and delivery through the nozzle.

18. The apparatus of claim 17, wherein the viscoelastic soft tip is disposed around the distal end of the elongated portion.

19. The apparatus of claim 17, wherein the pre-loaded lens is a non-modular lens.

20. The apparatus of claim 17, wherein the pre-loaded lens is a modular lens.

* * * * *